(12) United States Patent
Fidel et al.

(10) Patent No.: US 7,527,593 B2
(45) Date of Patent: May 5, 2009

(54) ACTIVE TEMPLATE GUIDE PLATE AND SYSTEM AND METHOD FOR UTILIZING SAME

(76) Inventors: Howard F. Fidel, 4 Algonquin Dr., Irvington, NY (US) 10533; Raul F. Gutierrez, 2470 Hammet Ave., Fort Lee, NJ (US) 07024

( * ) Notice: Subject to any disclaimer, the term of this patent is extended or adjusted under 35 U.S.C. 154(b) by 189 days.

(21) Appl. No.: 11/451,018

(22) Filed: Jun. 11, 2006

(65) Prior Publication Data
US 2007/0043291 A1 Feb. 22, 2007

Related U.S. Application Data

(60) Provisional application No. 60/689,654, filed on Jun. 11, 2005.

(51) Int. Cl.
*A51B 8/14* (2006.01)
(52) U.S. Cl. .............. 600/461; 600/1; 600/439; 604/65
(58) Field of Classification Search ............ 600/1, 600/3, 7, 8, 424, 461, 439
See application file for complete search history.

(56) References Cited

U.S. PATENT DOCUMENTS

| | | | |
|---|---|---|---|
| 5,871,448 A | 2/1999 | Ellard | |
| 6,387,034 B1 * | 5/2002 | Lee | 600/1 |
| 6,422,997 B1 | 7/2002 | Green et al. | |
| 6,428,504 B1 * | 8/2002 | Riaziat et al. | 604/65 |
| 6,539,247 B2 | 3/2003 | Spetz | |
| 6,572,526 B1 | 6/2003 | Ford | |
| 6,695,786 B2 * | 2/2004 | Wang et al. | 600/461 |
| 6,752,753 B1 | 6/2004 | Hoskins et al. | |
| 6,814,704 B2 * | 11/2004 | Weilandt | 600/461 |
| 6,869,390 B2 | 3/2005 | Elliott et al. | |
| 7,090,643 B2 | 8/2006 | Fidel et al. | |
| 2003/0229282 A1 * | 12/2003 | Burdette et al. | 600/439 |
| 2004/0158115 A1 | 8/2004 | Visacher et al. | |

\* cited by examiner

*Primary Examiner*—Long V Le
*Assistant Examiner*—Saurel J Selkin
(74) *Attorney, Agent, or Firm*—David Aker

(57) ABSTRACT

A guide plate for inserting, into a body, instruments, such as needles, used for medical purposes, comprising a plurality of openings for receiving an instrument; for each of the openings, a sensor arrangement for detecting presence of an instrument when an instrument is received in an opening; and reporting apparatus for reporting sensing of an instrument by each respective sensor arrangement. Use may be with an imaging system, including a display for an image of a portion of the body into which instruments are inserted. The imaging system can superimpose on the image an array corresponding to openings in the guide plate; a signal transmission means responsive to reports from respective reporting apparatus transmit output of the reporting apparatus to the imaging system. A display modification arrangement can modify elements of the array to indicate that an instrument has been inserted into a respective opening.

15 Claims, 4 Drawing Sheets

ACTIVE TEMPLATE GUIDE PLATE AND SYSTEM AND METHOD FOR UTILIZING SAME

This application claims priority under 35 U.S.C. §119 (e) from U.S. provisional patent application Ser. No. 60/689,654, filed on Jun. 11, 2005, which is incorporated herein by reference, in its entirety.

BACKGROUND OF THE INVENTION

1. Field of the Invention

This invention relates generally to an active template grid system. More particularly, it relates to an active template system for positioning medical implants. Still more particularly this invention relates to a template grid system for use with transrectal ultrasound imaging probes in brachytherapy and cryosurgery for cancerous prostate and related surgeries, where the template has sensors embedded in it to detect the presence of the seed-delivering, or freezing needles.

2. Background Art

As illustrated in FIG. 1 of U.S. Pat. No. 6,422,997, and in FIG. 1 of United States Patent Publication 20040152986 (the entire contents of which are incorporated by reference herein), brachytherapy is performed with the patient in the lithotomy position, using an ultrasound imaging probe placed in the rectum to monitor seed placement. A template grid arrangement or guide plate having openings at predefined positions of a coordinate grid thereon, of the general type illustrated in FIG. 3 of U.S. Pat. No. 6,387,034, which is kept in precise linear orientation with the ultrasound probe, must be accurately oriented adjacent the perineum in relation to the prostate, and locked in position throughout the procedure to achieve optimum seed placement. A cradle of the type illustrated in FIG. 17 of U.S. Pat. No. 6,752,753 is helpful in this regard. Precise and reproducible orientation and positioning of the ultrasound imaging probe in the rectum is a key element in both the calculations required for determining the number and distribution of radioactive seeds required for treatment and their subsequent placement using preloaded needles guided by the peritoneal template and real time ultrasound imaging.

Even with proper probe positioning, placement of the needles using the template grid needs to be accurate and precisely coordinated with the images from the probe and the patient's anatomy to have effective therapy. Keeping track of the actual needles inserted can also be problematic during the procedure.

SUMMARY OF THE INVENTION

It is an object of the invention to provide an apparatus and a method for using the apparatus, which keeps track of the actual insertions performed during a procedure.

It is a further object of the invention to keep track of the insertions automatically.

It is yet another object of the invention to assure that all of the insertions are at correct locations.

These objects and others are achieved in accordance with the invention by adding sensors to a template grid or guide plate to detect the presence of an insertion needle at each location. Indications of what locations, out of a multitude of locations, are to be used for insertion are provided. When an insertion has taken place, a change in the indication, or a further indication, is provided until the entire procedure has been completed.

In accordance with a first aspect, the invention is directed to a guide plate for inserting, into a body, needles used for medical purposes. The guide plate comprises a plurality of openings, each opening being for receiving a needle; for each of the openings, a sensor arrangement for detecting presence of a needle when a needle is received in an opening; and for each of the openings, reporting apparatus for reporting sensing of a needle by each a respective sensor arrangement.

Each of the sensors can comprise an electromagnetic source and an electromagnetic detector responsive to energy from the source, the source and the detector being disposed so that insertion of a needle into a respective opening blocks at least a portion of energy traveling from the light source to the detector. Alternatively, each of the sensors can comprise an inductor, and means for detecting a change in inductance of the inductor, the inductor being disposed so that insertion of a needle into a respective opening changes inductance of the inductor.

The guide plate can comprise a first wall and a second wall, which are generally parallel to one another, the openings being defined by tubes extending from the first wall to the second wall, and a respective sensor arrangement being disposed about respective ones of the tubes.

In accordance with the invention, the guide plate can be combined with an imaging system, the imaging system including a display for displaying an image of a portion of the body into which needles are to be inserted, the imaging system having means for superimposing on the image on the display an array corresponding to openings in the guide plate; signal transmission means responsive to reports from respective reporting apparatus for transmitting an output of the reporting apparatus to the imaging system; and a display modification arrangement responsive to signals from the signal transmission means for modifying elements of the array to indicate that a needle has been inserted into a respective opening in the guide plate. The imaging system can be an ultrasonic imaging system, the ultrasonic imaging system comprising an ultrasonic probe for contacting the body to display the portion of the body where the needles are inserted. The probe can be a transrectal probe, and the portion of the body that is imaged can include the prostate.

The signal transmission means can include at least one selected from the group consisting of an electrical cable, a radio link and an infrared link. The display modification arrangement can change color of a respective element of the array when a needle has been inserted into a respective opening in the guide plate.

A dosage calculation means for assisting in determining through which of the openings in the guide plate a needle should be placed for insertion into the body may also be provided.

The guide plate can be shaped with a portion for receiving a transrectal probe associated with an ultrasonic imaging system. Preferably, a cradle for carrying the transrectal probe and the guide plate is included.

The invention is also directed to a method for using the apparatus comprising the steps of connecting the apparatus to an imaging system having a capability for superimposing an array corresponding to the openings on an image of a portion of the body generated by the imaging system; inserting successive needles in indicated ones of the openings; and viewing modification of elements of the array as the needles are inserted to monitor which of the openings and corresponding locations in the body have needles inserted therein.

Another aspect of the invention is directed to an imaging system for a portion of a body, comprising an array generator for generating an array of symbols superimposed on an image of the portion of the body; an input for receiving data concerning which locations in the body corresponding to symbols of the array have undergone a change in status; and means for changing an indication associated with the symbols in the array to indicate which locations in the body have undergone a change in status. The system can further comprise a guide plate having an array of openings corresponding to the array of symbols; and a sensor arrangement for sensing insertion of an element into one of the openings and for providing an output indicative of the insertion; and means for changing the indication in response to the output. The system can be an ultrasonic imaging system.

The system can further comprise a transrectal probe for imaging a prostate; the guide plate being disposed to guide treatment needles into the prostate.

In accordance with yet another aspect, the invention is directed to a combination of components for operation with an imaging system, comprising a guide plate for inserting, into a body, needles used for medical purposes, the guide plate including a plurality of openings, each opening being for receiving a needle; for each of the openings, a sensor arrangement for detecting presence of a needle when a needle is received in an opening; and for each of the openings, reporting apparatus for reporting sensing of a needle by each a respective sensor arrangement; and a sensor reading module, responsive to the reporting apparatus for providing to the imaging system, data concerning which of the openings has a needle disposed therein. The data can be provided to the imaging system to change an indication representative of one of the openings on a display of the imaging system, when a needle is disposed in the one of the openings.

BRIEF DESCRIPTION OF THE DRAWINGS

The foregoing aspects and other features of the present invention are explained in the following description, taken in connection with the accompanying drawing, wherein.

DETAILED DESCRIPTION OF THE PREFERRED EMBODIMENT

Figure 1:
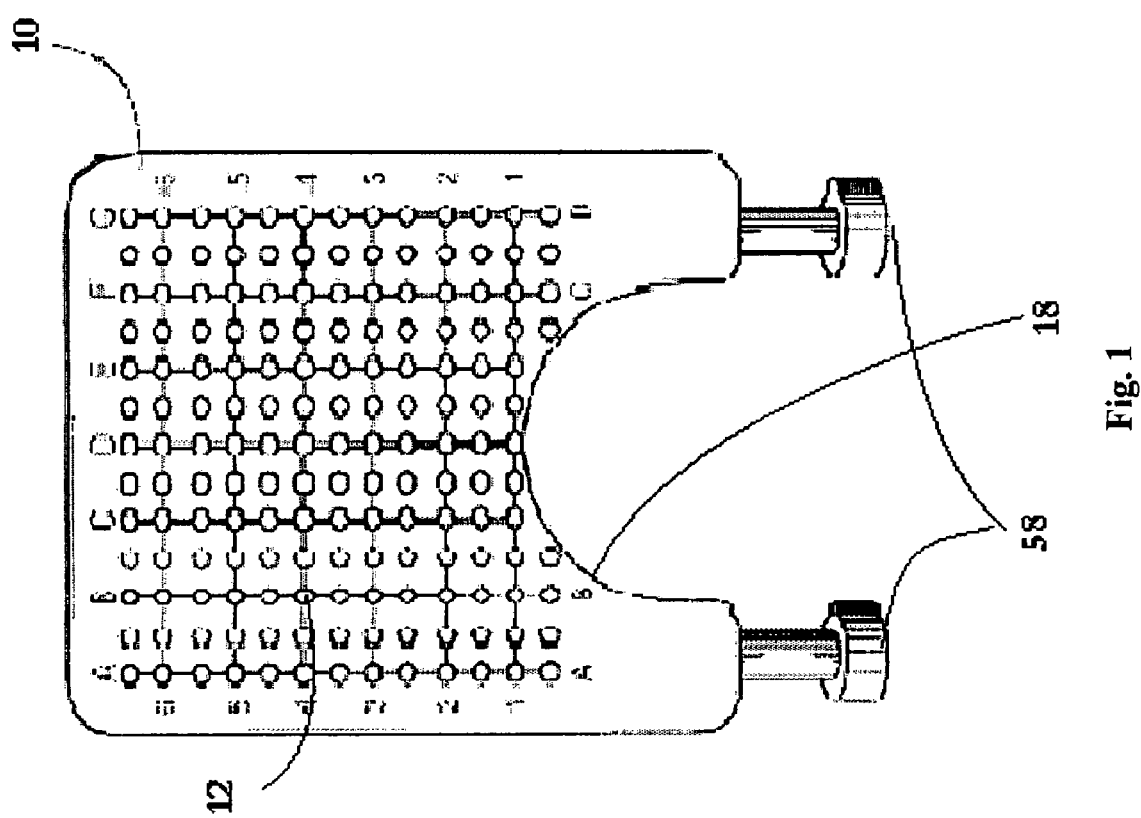
FIG. 1 is a plan view of a brachytherapy template or guide plate in accordance with the invention.

Referring to FIG. 1, there is shown a plan view of a template or guide plate 10 incorporating features of the present invention. Although the present invention will be described with reference to the single embodiment shown in the drawings, it should be understood that the present invention can be embodied in many alternate forms of embodiments. In addition, any suitable size, shape or type of elements or materials could be used. In view of the need for sterilization, guide plate 10 should be formed of a disposable material such as, for example, a plastic, or a metal or other material which can be sterilized.

As more fully described below with respect to FIG. 3, the ultrasound system used to guide the needles has a grid on the screen representing the locations of openings or through apertures 12 in guide plate 10 in FIG. 1. The ultrasound system can be associated with or contain a dosimetry program used to calculate the location of the radioactive seeds to be placed in the prostate, as is known in the art. The locations where needles are to be inserted are identified with a first color, preferably green. All other locations are identified by a second color, preferably red. The first location for the needle to be inserted blinks on the screen. After the system detects that a needle is inserted, the color of that location on the screen changes from green to red, indicating that a needle is already placed at that location. The next location that requires a needle insertion will flash green, until the next needle is inserted. When all the required needles are inserted, all the locations will have turned red.

Figure 2:
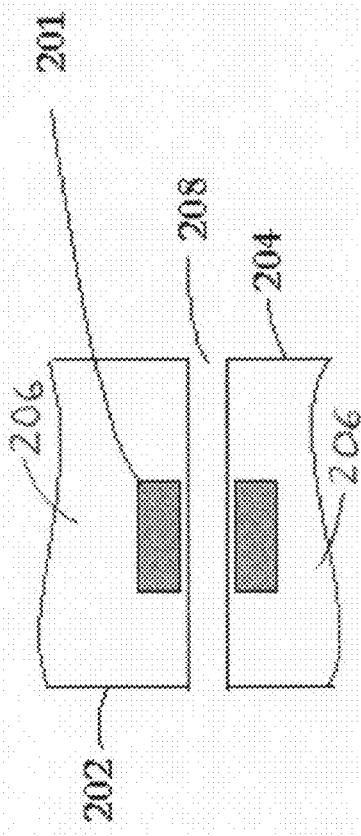
FIG. 2 is a partial sectional view of FIG. 1 illustrating a first embodiment of a sensor arrangement used in accordance with the invention.
Figure 2A:
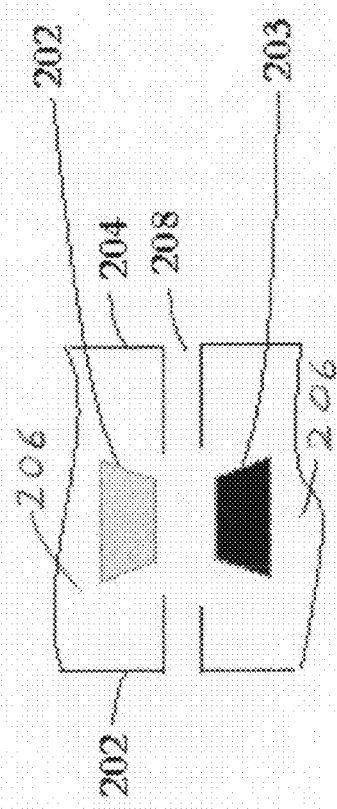
FIG. 2A is a partial sectional view of FIG. 1 illustrating a second embodiment of a sensor arrangement used in accordance with the invention.

Referring to FIG. 2 and FIG. 2A, the detection of a needle, which has been positioned in an opening or aperture 12, can be accomplished in several ways. In the embodiment of FIG. 2, the guide plate 10 may be comprised of a first wall 202 and a second wall 204, which are generally parallel to one another, with a space 206 between the walls. The openings 12 may be defined by tubes 208 extending from the first wall to the second wall. One approach is to have a photoelectric pair, including a light emitting diode (LED) 210, and a photoreceptor 212, located at each aperture 12 (at openings on opposite sides of the tube 208) in the grid of guide plate 10, so that the needle will block the light flow, and the system can then detect its presence.

In FIG. 2A, another embodiment uses a magnetic pickup. A coil 201 around each tube 208 senses the change in inductance of the coil as the needle passes through a aperture 12 in the guide plate 10.

Whatever their nature, the sensors associated with the apertures 12 may be electronically scanned, and the location of each needle passing through openings or apertures 12 in the guide plate 10 is easily detected.

Guide plate 10 has a curved cut out portion 18 through which the transrectal ultrasound probe extends in a direction generally perpendicular to the plane of guide plate 10. Both the transrectal ultrasound probe and the guide plate 10 are carried by a cradle, a pair of posts 58 extending from guide plate 10 being received in suitable openings in the cradle, as more fully illustrated in FIG. 3, below.

Figure 3:
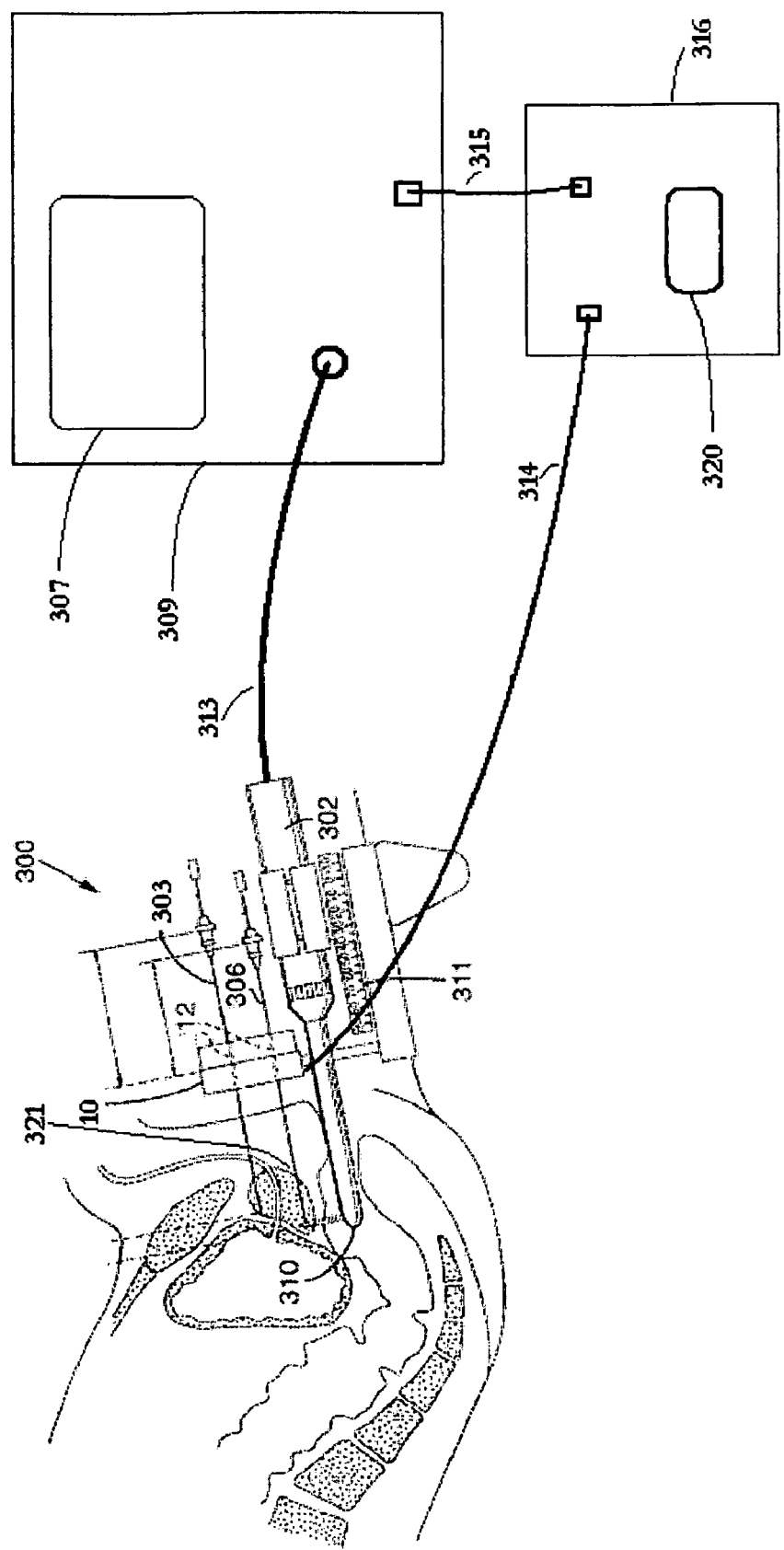
FIG. 3 is a diagram of a system which utilizes the present invention.

Referring to FIG. 3, and as discussed in U.S. Pat. No. 6,752,753, a conventional brachytherapy system including a cradle 300, has a stepping unit 302, one or more needles 306 and a corresponding number of stylets 303. Another example of a conventional stepping unit is disclosed in U.S. Pat. No. 5,871,448. The manner in which seeds are placed using this type of apparatus is discussed in detail in U.S. Pat. No. 6,752,753, and is incorporated herein by reference.

The guide plate 10 of the present invention may be supported by the stepping unit 302 at a position adjacent but spaced from the patient's body. The guide plate 10 having its array of openings or apertures 12, defining an x-y array, each of which openings or apertures 12 is sized to receive one of the needles 306. The apertures 12 extend in rows oriented in the x direction (i.e., perpendicular to the drawing page) and in columns oriented in the y direction (i.e., in or parallel to the 15 plane guide plate 10). Thus, each aperture 12 corresponds to a precise location in the x and y directions on a cross section of the prostate 321 parallel to the guide plate 10. Accordingly, for any specific aperture, a particular configuration of seeds for treating a portion of the prostate 321 at a position corresponding to that aperture can be used.

An ultrasound probe 310 coupled to the stepping unit 302 is inserted rectally to a depth adjacent a portion of a patient's prostate 321. The ultrasound probe 310 emits waves directed through the adjacent portion of the prostate 321 from which an ultrasonic cross-sectional image of that portion of the prostate 321 can be obtained. The stepping unit 302 incrementally moves the ultrasound probe to obtain ultrasound images of successive planes of the prostate or other organ or tissue. The stepper unit 302 includes a scale 311 oriented in the z direction that shows the depth of the ultrasonic probe 310 relative to a predetermined datum.

Ultrasound probe 310 is coupled to an ultrasonic imaging system 309 by a cable 313. System 309 and probe 310 may be of the kind described in United States Patent Publication 20040152986. System 309 includes an electronics module, the module having: excitation circuitry for exciting probe 310, receiving circuitry for processing signals received from probe 310, signal processing circuitry for processing signals from the receiving circuitry to produced processed image signals; and a display 307 for displaying the processed image signals.

Figure 3A:
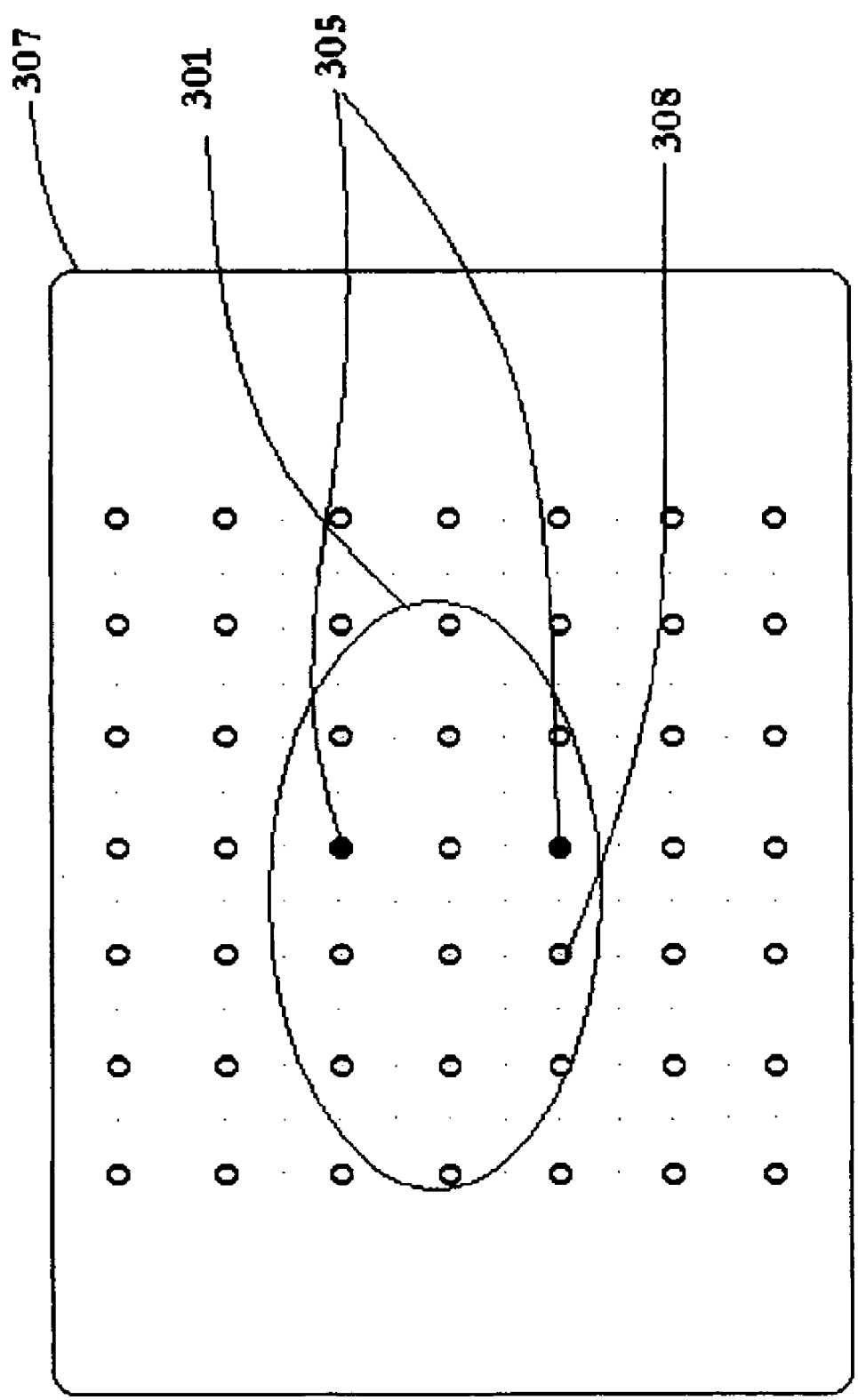
FIG. 3A is a view of the display of the system of FIG. 3.

In accordance with the invention, a cable 314 connects the sensors of guide plate 10 (described above with respect to FIG. 2 and FIG. 2A) with a sensor reading module 316, which monitors or scans the outputs of the sensors. Module 316 is in turn connected to system 309 by a cable 315, which supplies data concerning which apertures 12 have needles therein. This data is supplied to an array generating program, which superimposes an array of points, as illustrated in FIG. 3A, on the display 307. The program will change the color of the indicator for the apertures from, for example, green to red, indicating that the needle has already been placed.

While cable 314 connects the sensors of guide plate 10 to sensor reading module 316, it will be recognized that other signal transmission techniques, such as a radio or an infrared link may also be used.

The guide plate 10 and the sensor reading module 316 may be added to a standard ultrasonic imaging system, which has a software array generator added thereto, and input for receiving data from sensor reading module 316, to assemble a system in accordance with the invention. Thus, existing imaging systems may readily be adapted to implement the present invention, as described herein.

Referring to FIG. 3A, as noted above, the locations corresponding to the outline of the prostate 301 where needles are to be inserted are identified with a first color, preferably green (shown as gray 308 in Fig. 3A). All other locations are identified by a second color, preferably red (shown as black 305 in FIG. 3A). The first location for the needle to be inserted blinks on the screen. After the system detects that a needle is inserted, the color of that location on the screen changes from green to red, indicating that a needle is already placed at that location. The next location that requires a needle insertion will flash green, until the next needle is inserted. When all the required needles are inserted, all the locations will have turned red.

Thus, using the apparatus and method of the invention, the treating physician is immediately, continuously and accurately informed of which needles (and corresponding seeds in the case of brachytherapy) have been placed, and at which additional locations needles still need to be placed.

As noted above, imaging system 309 may have a software module 320 which assists in determining where needles are to be place in order to provide the proper treatment for a particular patient. Such software is described in U.S. Pat. No. 6,539,247.

While the present invention has been described with respect to an ultrasonic imaging system and apparatus used to treat the prostate, it will be understood that different types of imaging systems, such as, for example, x-ray systems may be used. Other procedures, on other parts of the body, which require accurate placement of instruments or sensors may be advantageously preformed with the apparatus and methods of the invention. Further, although the apertures in the guide plate, and corresponding display indicators have been shown to be arranged in a rectangular X-Y coordinate system, it will be understood that other coordinate systems may be useful for various portions of the body being treated, and the invention, as described herein, can be modified for use with such coordinate systems.

It should be understood that the foregoing description is only illustrative of the invention. Various alternatives and modifications can be devised by those skilled in the art without departing from the invention, which embraces all such alternatives, modifications and variances.

What is claimed is:

1. A guide plate for inserting, into a body, needles used for medical purposes, said guide plate comprising:
a plurality of openings, each opening being for receiving a needle,
a first wall and a second wall, which are generally parallel to one another, and define a generally hollow space between the first wall and the second wall, the openings being defined by tubes extending from the first wall to the second wall, and a respective sensor arrangement comprising a plurality of sensors, each of said plurality of sensors being disposed about a respective one of said tubes, the sensor arrangement being for detecting presence of a needle when a needle is received in an opening; and
for each of said openings, reporting apparatus for reporting sensing of a needle by each respective sensor arrangement.

2. The guide plate of claim 1, wherein each of said sensors comprises an electromagnetic source and an electromagnetic detector responsive to energy from said source, said source and said detector being disposed so that insertion of a needle into a respective opening blocks at least a portion of energy traveling from the source to the detector.

3. The guide plate of claim 1, wherein each of said sensors comprises an inductor, and means for detecting a change in inductance of said inductor, said inductor being disposed so that insertion of a needle into a respective opening changes inductance of said inductor.

4. The guide plate of claim 1, in combination with:
an imaging system, said imaging system including a display for displaying an image of a portion of the body into which needles are to be inserted, said imaging system having means for superimposing on said image on said display an array corresponding to openings in said guide plate;
wherein said reporting apparatus comprises:
signal transmission means for transmitting output to said imaging system representative of sensing of a needle by at least one of said plurality of sensors; and
a display modification arrangement responsive to signals from said signal transmission means for modifying elements of said array to indicate that a needle has been inserted into a respective opening in said guide plate.

5. The guide plate of claim 1, comprising a portion for receiving a transrectal probe associated with an ultrasonic imaging system, in combination with a cradle for carrying the transrectal probe and the guide plate.

6. A method for using the apparatus of claim 1, comprising the steps of:
connecting the apparatus of claim 1 to an imaging system having a capability for superimposing an array corresponding to said openings on an image of a portion of the body generated by said imaging system;

inserting successive needles in indicated ones of said openings; and viewing modification of elements of said array as said needles are inserted to monitor which of said openings and corresponding locations in the body have needles inserted therein.

7. The combination of claim 4, wherein said imaging system is an ultrasonic imaging system, said ultrasonic imaging system comprising an ultrasonic probe for contacting the body to display the portion of the body where said needles are inserted.

8. The combination of claim 4, wherein said signal transmission means includes at least one selected from the group consisting of an electrical cable, a radio link and an infrared link.

9. The combination of claim 4, wherein said display modification arrangement changes color of a respective element of said array when a needle has been inserted into a respective opening in said guide plate.

10. The combination of claim 7, wherein said probe is a transrectal probe, and the portion of the body that is imaged includes the prostate.

11. An imaging system for a portion of a body, comprising:
an array generator for generating an array of symbols superimposed on an image of said portion of the body;
an input for receiving data concerning which locations in the body corresponding to symbols of said array have undergone a change in status;
a guide plate having an array of openings corresponding to said array of symbols, said guide plate further comprising a first wall and a second wall, which are generally parallel to one another, and define a generally hollow space between the first wall and the second wall, the openings being defined by tubes extending from the first wall to the second wall, and a respective sensor arrangement comprising a plurality of sensors, each of said plurality of sensors being disposed about a respective one of said tubes;
a sensor arrangement for sensing insertion of an element into one of said openings and for providing an output indicative of said insertion; and
means for changing, in response to said output, an indication associated with said symbols in said array to indicate which locations in said body have undergone a change in status.

12. The system of claim 11, wherein said imaging system is an ultrasonic imaging system.

13. The system of claim 11, further comprising:
a transrectal probe for imaging a prostate; said guide plate being disposed to guide treatment needles into the prostate.

14. A combination of components for operation with an imaging system, comprising:
a guide plate for inserting, into a body, needles used for medical purposes, said guide plate including:
a plurality of openings in said guide plate, each opening being for receiving a needle, said guide plate comprising a first wall and a second wall, which are generally parallel to one another, and define a generally hollow space between the first wall and the second wall, the openings being defined by tubes extending from the first wall to the second wall, and a respective sensor arrangement comprising a plurality of sensors, each of said plurality of sensors being disposed about a respective one of said tubes;
said sensor arrangement being for detecting presence of a needle when a needle is received in an opening;
for each of said openings, reporting apparatus for reporting sensing of a needle by each a respective sensor arrangement; and
a sensor reading module, responsive to said reporting apparatus for providing to said imaging system, data concerning which of said openings has a needle disposed therein.

15. The combination of claim 14, wherein said data is of a form that when provided to said imaging system is used to change an indication representative of one of said openings on a display of said imaging system, when a needle is disposed in said one of said openings.

* * * * *